United States Patent [19]

Esteve-Soler

[11] Patent Number: 4,552,882
[45] Date of Patent: Nov. 12, 1985

[54] 7-(1-PYRROLYL) DERIVATIVES OF 1-ETHYL-1,4-DIHYDRO-4-OXOQUINOLINE-3-CARBOXYLIC ACIDS AND 1-ETHYL-1,4-DIHYDRO-4-OXO-1,8-NAPH-THYRIDINE-3-CARBOXYLIC ACIDS AND THEIR USE AS ANTIMICROBIAL AGENTS

[75] Inventor: José Esteve-Soler, Barcelona, Spain

[73] Assignee: Provesan, SA, Geneva, Switzerland

[21] Appl. No.: 622,647

[22] Filed: Jun. 20, 1984

[30] Foreign Application Priority Data

Jul: 6, 1983 [FR] France ............................ 83 11250
Feb. 13, 1984 [FR] France ............................ 84 02145

[51] Int. Cl.$^4$ ............................................. A61K 31/44
[52] U.S. Cl. ................................. 514/300; 546/123; 546/156
[58] Field of Search ............... 546/123, 156; 424/256, 424/258

[56] References Cited

U.S. PATENT DOCUMENTS 4,341,784 7/1982 Matsumoto et al. ............... 424/256

OTHER PUBLICATIONS

M. Artico, F. Corelli, S. Massa, G. Stefancich, S. Panico, N. Simonetti, Farmaco Ed. Sci., 1984, 39 (11), 910–924.

Acta Chem. Scand., 6, 867–874 (1952), Niels Elming and Niels Clauson-Kaas.

Primary Examiner—Henry R. Jiles
Assistant Examiner—Barbara Cassatt
Attorney, Agent, or Firm—Pennie & Edmonds

[57] ABSTRACT

The present invention relates to new derivatives of 7-(1-pyrrolyl)-1-ethyl-1,4-dihydro-4-oxoquinoline-3-carboxylic acid and 7-(1-pyrrolyl)-1-ethyl-1,4-dihydro-4-oxo-1,8-naphthyridine-3-carboxylic acid of general formula I:

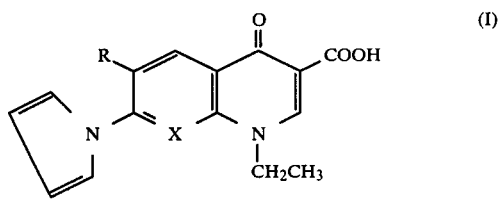

in which:
X represents a carbon atom or a nitrogen atom, and
R represents a hydrogen atom or a fluorine atom, as well as their physiologicaly acceptable alkali metal salts or alkaline earth metal salts. The derivatives of the present invention are advantageously used as antimicrobial agents, espcially as anti-bacterial and anti-fungal agents.

8 Claims, No Drawings

7-(1-PYRROLYL) DERIVATIVES OF 1-ETHYL-1,4-DIHYDRO-4-OXOQUINOLINE-3-CARBOXYLIC ACIDS AND 1-ETHYL-1,4-DIHYDRO-4-OXO-1,8-NAPHTHYRIDINE-3-CARBOXYLIC ACIDS AND THEIR USE AS ANTIMICROBIAL AGENTS

FIELD OF THE INVENTION

The present invention relates to new derivatives of 1-ethyl-1,4-dihydro-4-oxoquinoline-3-carboxylic acid and 1-ethyl-1,4-dihydro-4-oxo-1,8-naphthyridine-3-carboxylic acid, both substituted in position 7 by the 1-pyrrolyl group, and also to their preparation and application as drugs.

SUMMARY OF THE INVENTION

The new derivatives which are the subject of the present invention correspond to the general formula I:

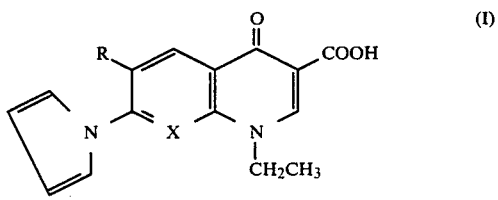

in which:

X represents a carbon atom or a nitrogen atom, and R represents a hydrogen atom or a fluorine atom.

The present invention also relates to the physiologically acceptable alkali metal salts or alkaline earth metal salts of the compounds of general formula I.

The derivatives of general formua I and their salts have useful antimicrobial pharmacological properties, notably antibacterial and fungistatic properties.

The new compounds have powerful antibacterial activity in respect of both gram positive and gram negative bacteria.

DETAILED DESCRIPTION

The new derivatives of general formula I can be prepared according to the invention by means of the following reaction scheme:

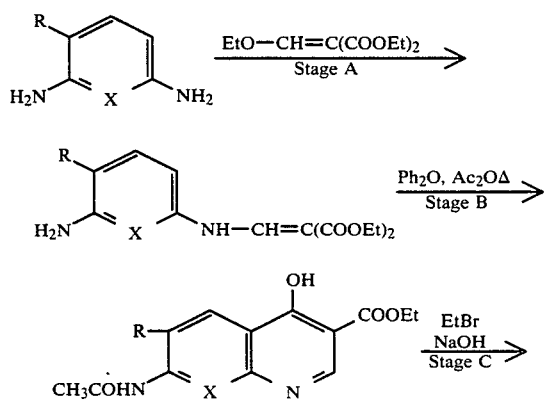

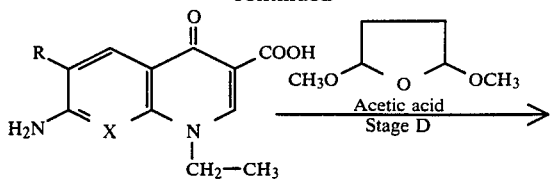

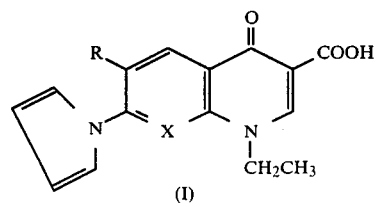

where X and R have the meanings given above.

In stage A, the appropriate diamine is condensed directly with diethyl ethoxymethylenemalonate to give the ethyl monoaminomethylenemalonate by elimination of alcohol. During stage B, the compound is cyclized by heating either in the absence of solvent, or employing an appropriate solvent which acts as a thermal exchanger such as, for example, benzene, toluene, xylene, tetralin, nitrobenzene, dichlorobenzene, diphenyl ether or biphenyl, or, furthermore, a mixture of these solvents.

The reaction temperature is between 150° C. and 250° C., preferably between 180°–230° C. By using certain catalysts, it is possible to effect the cyclization at much lower temperatures. Among the appropriate catalysts, polyphosphoric ester, polyphosphoric acid, phosphoric anhydride, etc., may be mentioned by way of example. With these catalysts, temperatures generally between 60°–170° C. are employed, or better still, between 75° C. and 150° C.

During stage C, the N-alkylated compounds are then prepared. The alkylation can be performed using one of the conventional alkylating agents, which include, among others, the alkyl halides, the dialkyl sulfates, the alkyl sulfonates, etc.

In general, the reaction is performed in the presence of an alkali and in a solvent which is inert with respect to the reaction. The solvents, can, in particular, consist of water, methanol, ethanol, acetone, dioxane, benzene, dimethylformamide, dimethylsulfoxide, as well as mixtures of these solvents.

The preferred alkalis which can be used are the alkali metal hydroxides, such as sodium hydroxide and potassium hydroxide, or else alkali metal carbonates, such as sodium carbonate or potassium carbonate.

It should be noted that during stage C, the alkylation process is accompanied by a hydrolysis of the carboxylic ester since the medium is distinctly alkaline, so that the corresponding carboxylic acids are obtained.

In the final stage D, the pyrrole nucleus is grafted according to the method of Clauson-Kaas, Acta Chem. Scand. 6, 667 and 867 (1952), by reaction of the amine with dimethoxytetrahydrofuran by refluxing for a half hour in acetic acid medium.

In the particular case of the preparation of 1-ethyl-1,4-dihydro-4-oxo-6-fluoro-7-(1-pyrrolyl)-1,8-naphthyridine-3-carboxylic acid, it should be noted that the synthesis intermediate necessary for performing the grafting of the pyrrole nucleus in stage D is new, and, by virtue of this, also forms a part of the present invention.

In this particular case, this reaction stage D is schematized as follows:

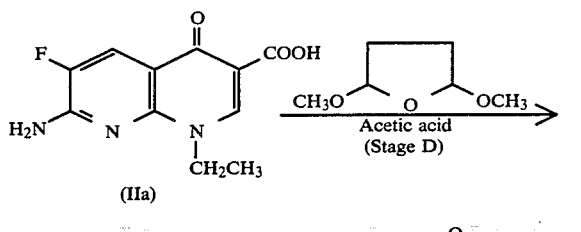

This synthesis intermediate can be prepared for example from 1-ethyl-1,4-dihydro-4-oxo-6-fluoro-7-chloro-1,8-naphthyridine-3-carboxylic acid (for example, described in European Patent Application No. 0,027,752) according to the following reaction scheme:

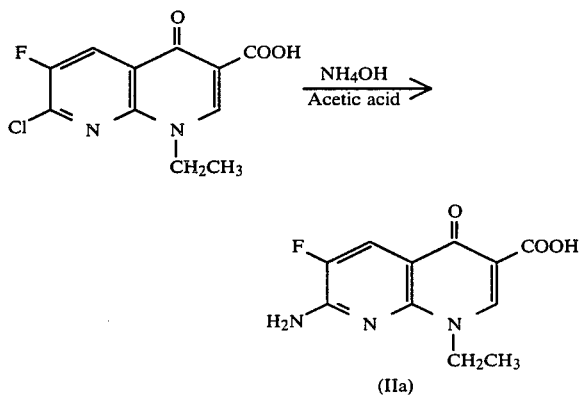

In the following examples, the preparation of new derivatives according to the invention will be indicated, as well as corresponding starting materials and intermediate products. Some typical forms of using the compounds will also be described, for the different fields of application.

The examples below, which are given simply by way of illustration, must not, however, be taken to limit in any way the scope of the invention.

EXAMPLE 1

Preparation of diethyl 3-aminoanilino-methylenemalonate (stage A)

10.8 Grams of m-phenylenediamine are dissolved in 80 ml of ethyl alcohol, 21.6 grams of diethyl ethoxymethylenemalonate are added and the mixture is heated under reflux for 40 minutes. After filtration hot, 50 ml of water are added and the mixture is left for 24 to 36 hours at room temperature with stirring. The precipitate formed is filtered off, washed with an ethanol/water (1:1) mixture and dried at 60° C. The product is recrystallized in a benzene/hexane (2:1) mixture and 10.5 grams of a solid are obtained, of melting point 71°–74° C.

Preparation of ethyl 7-acetamido-4-hydroxy-3-quinolinecarboxylate (stage B)

10.5 Grams of diethyl 3-aminoanilino-methylenemalonate are dissolved in 80 ml of diphenyl oxide, 8 ml of acetic anhydride are added and the mixture is gradually heated to 250° C. and maintained under reflux for 10 minutes. The mixture is allowed to cool, 20 ml of ethanol are added and the solid is filtered off and washed with ethanol. The product is recrystallized in dimethylformamide and 4.6 grams of a solid are obtained, of melting point 295° to 300° C.

Preparation of 7-amino-1-ethyl-1,4-dihydro-4-oxo-3-quinolinecarboxylic acid (stage C)

4.6 Grams of ethyl 7-acetamido-4-hydroxy-3-quinolinecarboxylate are dissolved in 15 ml of 10% NaOH, 60 ml of H$_2$O and 100 ml of ethanol, and 5 ml of ethyl bromide are added. The mixture is left under reflux for 4 hours, then the excess of ethyl bromide and ethanol is evaporated off, and 10 ml of 10% NaOH are then added. The mixture is heated under reflux for 2 hours, allowed to cool, acidified with HCl, filtered and treated with ethanol at 70° C. The product is filtered off and recrystallized in a dimethylformamide/water (1:1) mixture. 1.0 Gram of a solid is obtained, of melting point 304°–307° C.

Preparation of 7-(1-pyrrolyl)-1-ethyl-1,4-dihydro-4-oxo-3-quinolinecarboxylic acid (stage D)

0.3 Gram of 7-amino-1-ethyl-1,4-dihydro-4-oxo-3-quinolinecarboxylic acid is suspended in 10 ml of acetic acid, 0.17 gram of dimethoxytetrahydrofuran is added and the mixture is heated until the solid has dissolved. The mixture is filtered, and water is added to the filtrate until it becomes turbid. The filtrate is allowed to cool, and the precipitate obtained is filtered off and washed with ethanol. 0.12 gram of a solid is obtained, of melting point 235°–238° C.

Spectroscopic data:

$^1$H NMR,δ,[DMSO (d$_6$)]: 1.46 (t,3H); 4.57 (q, 2H); 6.23 (m, 2H); 7.43 (m, 2H); 7.59 [d(J=8 Hz), 1H]; 7.68 (s, 1H); 8.18 [d(J=8 Hz), 1H]; 8.76 (s, 1H); 14.80 (s, 1H). IR (KBr): 1620, 1720 cm$^{-1}$.

EXAMPLE 2

Preparation of 4-fluoro-m-phenylenediamine

To a solution of 9 grams of SnCl$_2$.2H$_2$O in 12 ml of concentrated HCl, are added in a single batch, with stirring, 1.6 grams of 4-fluoro-3-nitroaniline, which dissolves as a brisk reaction occurs, the temperature reaching 95° to 100° C. The reaction mixture is allowed to cool to room temperature, and poured into 70 ml of 50% NaOH solution in ice, so that the temperature remains below 20° C. The resultant strongly alkaline solution is extracted 3 times with 50 ml of ethyl ether. The ethyl ether extracts are combined, washed with 30 ml of distilled water and dried with anhydrous sodium sulfate. The ethyl ether solution is evaporated to dryness and 1.2 gram of a dark colored oil is obtained.

Preparation of diethyl 4-fluoro-3-aminoanilinomethylenemalonate (stage A)

A solution of 2.16 grams of diethyl ethoxymethylenemalonate and 1.26 gram of 4-fluoro-m-phenylenediamine in 40 ml of ethanol is heated under reflux for 30 minutes, and 15 ml of water are added while the mixture is hot. The mixture is allowed to cool and the precipitate formed filtered off and washed with an ethanol/H$_2$O (1:1) mixture. The product is dried at 60° C. and recrystallized in a benzene/hexane (2:1) mixture, giving 1.6 gram of crystals, of melting point 100°–102° C.

Preparation of ethyl 7-acetamido-4-hydroxy-6-fluoro-3-quinolinecarboxylate (stage B)

1.6 Gram of diethyl 4-fluoro-3-aminoanilinomethylenemalonate is dissolved in a mixture of 8 ml of diphenyl oxide and 1 ml of acetic anhydride, and the mixture is heated gradually to 250° C., at which temperature a precipitate appears. The mixture is left under reflux for 10 minutes and allowed to cool. 5 ml of ethanol are added and the solid is filtered off and washed with ethanol. The product is recrystallized in dimethylformamide and 1 gram of a solid is obtained, of melting point 320° C.

Preparation of 6-fluoro-7-amino-1-ethyl-1,4-dihydro-4-oxo-3-quinolinecarboxylic acid (stage C)

1.5 ml of ethyl bromide is added to a solution of 1 gram of ethyl 7-acetamido-4-hydroxy-6-fluoro-3-quinolinecarboxylate in 25 ml of water, 60 ml of ethanol and 2.5 ml of 10% sodium hydroxide solution, and the mixture is maintained under reflux for 4 hours. The mixture is then concentrated to half its volume, 5 ml of 10% sodium hydroxide solution are added and refluxing is maintained for 1 hour. The mixture is allowed to cool and is acidified with hydrochloric acid, and the precipitate formed is filtered off. The precipitate is washed with water, dried, and recrystallized in a dimethylformamide/water (10:1) mixture.

0.65 Gram of a solid is obtained, which melts at 298°–300° C. with decomposition.

Preparation of 6-fluoro-7-(1-pyrrolyl)-1-ethyl-1,4-dihydro-4-oxo-3-quinolinecarboxylic acid (stage D)

2.5 Grams of 6-fluoro-7-amino-1-ethyl-1,4-dihydro-4-oxo-3-quinolinecarboxylic acid are suspended in 15 ml of acetic acid, and 1.32 gram of dimethoxytetrahydrofuran is added; the mixture is heated gradually until the solid dissolves, and is then allowed to cool. The precipitate formed is filtered off and washed with ethanol. The product is recrystallized in acetonitrile, and 1.4 gram of needles is obtained, of melting point 251°–252° C.

Spectroscopic data:

$^1$H NMR,δ, [DMSO (d$_6$)]: 1.48 (t,3H); 4.62 (q,2H); 6.38 (t,2H); 7.34 (q,2H); 7.99 [d(J=6.1 Hz),1H]; 8.10 [d(J=11.4 Hz),1H]; 8.92 (s, 1H); 14.65 (s,1H).
IR (KBr): 1620, 1720 cm$^{-1}$.

EXAMPLE 3

Preparation of 1-ethyl-1,4-dihydro-4-oxo-7-(1-pyrrolyl)-1,8-naphthyridine-3-carboxylic acid (stage D)

4.6 Grams of 1-ethyl-1,4-dihydro-4-oxo-7-amino-1,8-naphthyridine-3-carboxylic acid (U.S. Pat. No. 3,149,104) and 2.7 grams of 2,5-dimethoxytetrahydrofuran are placed under reflux for 30 minutes in 70 ml of glacial acetic acid. The mixture is allowed to cool then left for 8 hours at 5° C., and a precipitate is obtained which, when filtered off and recrystallized in acetonitrile, gives 4.3 grams of needles, of melting point 230°–232° C.

Spectroscopic data:

$^1$H NMR, δ, [DMSO (d$_6$)]: 1.47 (t,3H); 4.57 (q,2H); 6.30 (m,2H ); 7.70 (m,2H); 7.80 [d(J=8.4 Hz), 1H]; 8.53 [d(J=8.4 Hz), 1H]; 8.95 (s,1H); 14.62 (s, 1H).
IR (KBr): 1625, 1720 cm$^{-1}$.

EXAMPLE 4

Preparation of 1-ethyl-1,4-dihydro-4-oxo-6-fluoro-7-(1-pyrrolyl)-1,8-naphthyridine-3-carboxylic acid (stage D)

1.4 gram of 1-ethyl-1,4-dihydro-4-oxo-6-fluoro-7-amino-1,8-naphthyridine-3-carboxylic acid, having a melting point of 299°–303° C. (decomposes) and giving the following spectroscopic data:

$^1$H NMR,δ, [CF$_3$COOH]: 1.70 (t,3H); 4.83 (q,2H); 8.10 [d(J=9.4 Hz),1H]; 9.11 (s,1H).
IR (KBr): 1650, 1720, 3320, 3425 cm$^{-1}$, is suspended in 20 ml of a mixture of acetic acid and dimethylformamide (1:1) 0.8 Gram of 2,5-dimethoxytetrahydrofuran is added, and the mixture is heated under reflux for 10 minutes. After being left to cool, the mixture is left standing for 8 hours at 5° C., and a precipitate is obtained which, when filtered off and recrystallized in acetone, gives 0.95 gram of needle-shaped crystals, of melting point 257°–259° C.

Spectroscopic data:

$^1$H NMR,δ, [CF$_3$COOH]: 1.67 (t,3H); 4.88 (q,2H); 6.36 (m,2H); 7.68 (m,2H); 8.40 [d(J=11 Hz),1H]; 9.23 (s,1H).
IR (KBr): 1625, 1725 cm$^{-1}$.

The starting compound can be prepared as follows:

1 Gram of 1-ethyl-1,4-dihydro-4-oxo-6-fluoro-7-chloro-1,8-naphthyridine-3-carboxylic acid (for example, described in European Patent Application No. 0,027,752) is mixed with 25 ml of concentrated ammonia solution containing 20% of ethanol. The mixture is maintained in a sealed tube for 4 hours at 120°–125° C. The mixture is cooled, and acetic acid added until the pH is slightly acid, when the precipitate formed is filtered off and washed with water. The product is dried, 0.8 gram of 1-ethyl-1,4-dihydro-4-oxo-6-fluoro-7-amino-1,8-naphthyridine-3-carboxylic acid being obtained, of melting point 299°–303° C.

Antimicrobial pharmacological activity (G. L. Daquet and Y. A. Chabbect, Techniques en bactériologie (Bacteriological techniques), vol. 3, Flammarion Medecine Sciences, Paris, 1972 and W. B. Hugo and A. D. Rusell, Pharmaceutical Microbiology, Blackwell Scientific Publications, London, (1977)).

Culture medium and solvent:

Antibiotic medium no. 1 (seed agar) (Oxoid CM 327)
Tryptone-soya broth (Oxoid CM 129)
Ringer's physiological solution ¼ (oxoid BR 52) Dextrose agar (BBL-11165) 0.1 N NaOH Microorganisms:

"Bacillus subtilis" ATCC 6633
"Citrobacter freundii" ATCC 11606
"Enterobacter aerogenes" ATCC 15038
"Enterobacter cloacae" CHSP 20
"Escherichia coli" ATCC 10536
"Escherichia coli" R-1513
"Klebsiella pneumoniae" ATCC 10031
"Micrococcus flavus" ATCC 10240
"Proteus mirabilis" ATCC 4675
"Proteus morganii" CHSP 16
"Pseudomonas aeruginosa" ATCC 25115
"Pseudomonas aeruginosa" ADSA 47
"Salmonella typhimurium" AMES 98
"Salmonella typhimurium" AMES 100
"Sarcina Lutea" ATCC 9341
"Serratia marcescens" ATCC 13880
"Shigella flexnerii"
"Staphylococcus aureus" ATCC 5488/23
"Staphylococcus aureus" ATCC 25178
"Streptococcus faecalis" ATCC 10541

Preparation of the inoculations

Each of the microorganisms is seeded by streaking in tubes of Antibiotic medium No. 1 (seed agar), which are then incubated at 37° C. for 20 hours. Using a culture loop, the cultures are then seeded in tryptone-soya broth and incubated at 37° C. for 20 hours. The culture obtained is diluted to ¼ with Ringer's physiological solution, so as to obtain a standardized suspension of $10^7$–$10^9$ cfu/ml for each organism.

Preparation of the medium containing the derivatives of general formula I

Starting from a solution of 1,000 μg/ml in 0.1 N NaOH, each product is diluted in Dextrose agar (previously melted and maintained at 50° C.), with successive dilutions so as to obtain the following concentrations: 64—32—16—8—4—2—1—0.5—0.25—0.125 μg of derivative/ml medium.

For each product, the solution of each concentration is subsequently distributed into Petri dishes 10 cm in diameter, with 10 ml of medium per dish and the same number of dishes as microorganisms to be tested.

As soon as the medium has cooled, the dishes are seeded with the inoculations using 0.4 ml of inoculation per dish. They are spread with a Driglasky loop and the supernatant is removed. The seeded dishes are incubated at 37° C. for 20 hours.

Results

The results obtained are shown in Table I. The products of Examples 1, 2 and 4 have an "in vitro" activity greater than that of pipemidic acid, with respect to both enterobacteriaceae (Pseudomonas aeruginosa) and gram-positive cocci. The derivative of Example 3 has an activity of the same order as that of pipemidic acid with respect to gram-negative microorganisms and a greater activity with respect to gram-positive cocci.

TABLE I

| | MIC "in vitro" compared to pipemidic acid Concentrations are given in μg/ml. | | | | |
|---|---|---|---|---|---|
| MICROORGANIAMS | Compound of Example 1 | Compound of Example 2 | Compound of Example 3 | Compound of Example 4 | PIPEMIDIC ACID |
| Bacillus subtilis ATCC 6633 | <0.125 | <0.125 | 0.25 | 0.03 | 8 |
| Citrobacter freundii ATCC 11606 | 16 | 8 | 32 | 4.00 | 4 |
| Enterobacter aerogenes ATCC 15038 | >64 | 8 | >64 | 4.00 | 32 |
| Enterobacter cloacae CHSP 20 | 16 | 1 | 8 | 2.00 | 8 |
| Escherichia coli ATCC 10536 | 4 | 1 | 8 | 0.12 | 2 |
| Escherichia coli R-1513 | 16 | 4 | 16 | 4.00 | 16 |
| Klebsiella pneumoniae ATCC 10031 | 1 | 0.5 | 4 | 1.00 | 2 |
| Micrococus flavus ATCC 10240 | 16 | 8 | 4 | 1.00 | >64 |
| Proteus mirabilis ATCC 4675 | 16 | 4 | >64 | 8.00 | 16 |
| Proteus morganii CHSP 16 | 8 | 2 | 8 | 4.00 | 8 |
| Pseudomonas aeruginosa ATCC 25115 | >64 | 16 | >64 | 32.00 | 32 |
| Pseudomonas aeroginosa ADSA 47 | >64 | 64 | >64 | >64.00 | 32 |
| Salmonella typhimurius AMES 98 | 0.5 | <0.125 | 0.5 | 0.12 | 4 |
| Salmonella typhimurius AMES 100 | 4 | 0.5 | 8 | 0.50 | 8 |
| Sarcina lutea ATCC 9341 | 16 | 16 | 8 | 4.00 | >64 |
| Serratia marcescens ATCC 13880 | 8 | 2 | 16 | 2.00 | 16 |
| Shigella flexnerii | 8 | 2 | 16 | 2.00 | 4 |
| Staphylococcus aureus ATCC 5488/23 | 1 | 0.25 | 8 | 0.50 | 64 |
| Staphylococcus aureus ATCC 25178 | 1 | 0.25 | 4 | 0.50 | 64 |
| Streptococcus faecalis ATCC 10541 | 16 | 1 | 32 | 8.00 | >64 |

Acute toxicity in mice

To determine this toxicity, C.F.L.P. strain albino mice of both sexes, weighing between 19 and 25 grams, have been used as experimental animals. After an 18 hour fast period with water "ad libitum" the derivatives which are the subjects of the present invention are administered intraperitoneally in 5% suspension in gum arabic. The volume of suspension administered has in all cases been 0.4 ml/20 grams (20 ml/kg), changing the concentration of the suspension according to the dose administered.

One hour after the administration of the derivatives, the animals are supplied with Panlab standard rat-mouse feed. The period of observation of mortality has been 7 days. None of the products has shown any differences between the sexes in respect of mortality.

The results obtained are shown in Table II.

TABLE II

| Derivatives | Administration route | $LD_{50}$ mg/kg |
|---|---|---|
| Example 1 | i.p. | >800 |
| Example 2 | i.p. | >1,600 |

TABLE II-continued

| Derivatives | Administration route | LD$_{50}$ mg/kg |
| --- | --- | --- |
| Example 3 | i.p. | 900 |
| Example 4 | i.p. | >1,000 |
| Nalidixic acid | i.p. | 600 |
| Pipemidic acid | i.p. | >1,600 |

In view of their good pharmacological properties, the derivatives of general formula I are thus capable of being utilized in human and/or veterinary medicine, for the treatment of acute, chronic and recurrent systemic or localized infections, caused by Gram-positive and Gram-negative microorganisms which are sensitive to the products which are the subject of the present invention, in the gastrointestinal or genito-urinary tract, the respiratory apparatus, the skin and the soft tissues, as well as neurological and odonto-stomatological infections.

In human therapy, the dose suggested for the derivatives of the present invention is approximately between 400 and 1,200 mg/day for an adult, administered, for example, in the form of tablets or capsules. This dosage can, however, vary according to the severity of the ailment.

By way of example, two particular medicinal forms of the derivatives which are the subject of the present invention are shown below.

| Example of formula as a tablet | |
| --- | --- |
| 6-fluoro-7-(1-pyrrolyl)-1-ethyl-1,4-dihydro-4-oxo-3-quinolinecarboxylic acid | 0.400 g |
| Carboxymethyl starch | 0.018 g |
| Polyvinylpyrrolidone K29-32 | 0.030 g |
| Microcrystalline cellulose | 0.146 g |
| Colloidal silica | 0.003 g |
| Magnesium stearate | 0.003 g |
| | 0.600 g |
| Example of formula as a tablet | |
| 6-fluoro-7-(1-pyrrolyl)-1-ethyl-1,4-dihydro-4-oxo-3-quinolinecarboxylic acid | 0.400 g |
| Microcrystalline cellulose | 0.0356 g |
| Colloidal silica | 0.0022 g |
| Magnesium stearate | 0.0022 g |
| | 0.440 g |

I claim:

1. A compound of the general formula:

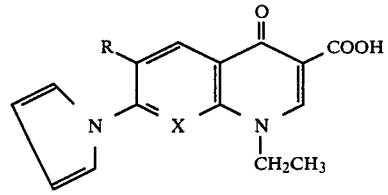

in which
X represents a carbon atom or a nitrogen atom, and
R represents a hydrogen atom or a fluorine atom;
and physiologically acceptable alkali metal salts or alkaline earth metal salts thereof.

2. 7-(1-Pyrrolyl)-1-ethyl-1,4-dihydro-4-oxoquinoline-3-carboxylic acid corresponding to the general formula I as claimed in claim 1.

3. 7-(1-Pyrrolyl)-6-fluoro-1-ethyl-1,4-dihydro-4-oxoquinoline-3-carboxylic acid corresponding to the general formula I as claimed in claim 1.

4. 7-(1-Pyrrolyl)-1-ethyl-1,4-dihydro-4-oxo-1,8-naphthyridine-3-carboxylic acid corresponding to the general formula I as claimed in claim 1.

5. 7-(1-Pyrrolyl)-6-fluoro-1-ethyl-1,4-dihydro-4-oxo-1,8-naphthyridine-3-carboxylic acid corresponding to the general formula I as claimed in claim 1.

6. A compound of the formula:

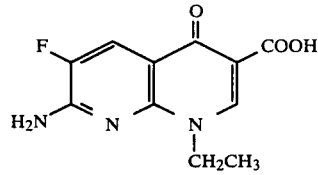

7. An antimicrobial composition comprising an antimicrobially therapeutically effective amount of a compound of formula:

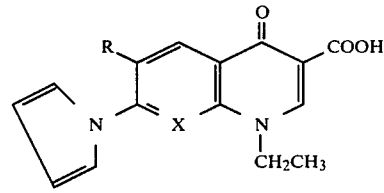

in which
X represents a carbon atom or a nitrogen atom, and
R represents a hydrogen atom or a fluorine atom, or a physiologically acceptable alkali metal salt or alkaline earth metal salt thereof, and a pharmaceutically acceptable vehicle therefor.

8. The antimicrobial composition according to claim 7 wherein the pharmaceutically acceptable vehicle is selected from the group consisting of: carboxymethyl starch, polyvinylpyrrolidone, cellulose, colloidal silica, magnesium stearate and mixtures containing any one or more of such pharmaceutically acceptable vehicles.

* * * * *